(12) United States Patent
Nestenborg et al.

(10) Patent No.: US 9,314,585 B2
(45) Date of Patent: Apr. 19, 2016

(54) CATHETER ASSEMBLY

(75) Inventors: Daniel Nestenborg, Brännö (SE); Andrea Schmid, Mölnlycke (SE)

(73) Assignee: ASTRA TECH AB, Molndal (SE)

( * ) Notice: Subject to any disclaimer, the term of this patent is extended or adjusted under 35 U.S.C. 154(b) by 0 days.

(21) Appl. No.: 12/427,686

(22) Filed: Apr. 21, 2009

(65) Prior Publication Data

US 2009/0200187 A1  Aug. 13, 2009

Related U.S. Application Data

(62) Division of application No. 10/487,912, filed as application No. PCT/SE03/00681 on Apr. 29, 2003, now Pat. No. 8,740,863.

(30) Foreign Application Priority Data

Apr. 30, 2002  (SE) ...................... 0201330

(51) Int. Cl.
*A61M 5/32* (2006.01)
*A61M 25/00* (2006.01)

(52) U.S. Cl.
CPC ......... *A61M 25/002* (2013.01); *A61M 25/0017* (2013.01); *A61M 2025/0046* (2013.01); *A61M 2210/1085* (2013.01); *Y10T 156/10* (2015.01)

(58) Field of Classification Search
CPC ............ A61M 25/002; A61M 2025/0046; A61M 2025/0062; A61M 2210/1078; A61M 25/0017; A61M 25/0111; A61B 19/045; A61L 29/085
USPC .................. 604/265, 171, 172, 263
See application file for complete search history.

(56) References Cited

U.S. PATENT DOCUMENTS

| | | | |
|---|---|---|---|
| 2,997,043 A | 8/1961 | Flynn | |
| 3,345,988 A * | 10/1967 | Vitello | ............... A61M 25/002 206/364 |
| 3,648,704 A | 3/1972 | Jackson | |
| 3,854,483 A | 12/1974 | Powers | |
| 3,967,728 A | 7/1976 | Gordon et al. | |
| 4,811,847 A * | 3/1989 | Reif | .................... A61B 19/045 206/210 |
| 5,582,599 A | 12/1996 | Daneshvar | |
| 6,059,107 A | 5/2000 | Nosted et al. | |
| 6,090,075 A | 7/2000 | House | |
| 6,634,498 B2 * | 10/2003 | Kayerød | ............... A61L 29/085 206/210 |

(Continued)

FOREIGN PATENT DOCUMENTS

| | | |
|---|---|---|
| DE | 3223535 A1 | 3/1983 |
| DE | 43 12 353 A1 | 11/1993 |

(Continued)

*Primary Examiner* — Phillip Gray
(74) *Attorney, Agent, or Firm* — Birch, Stewart, Kolasch & Birch, LLP

(57) ABSTRACT

A catheter assembly includes a catheter, part of which forms an insertable length to be inserted through a body opening and a catheter receptacle to accommodate at least part of the catheter such that an insertable portion of the catheter is enclosed but part of the catheter is left outside of the receptacle. Also disclosed is a method for producing a catheter assembly which includes providing a receptacle having an opening, providing a catheter which has a catheter tube and a connector on one end thereof, arranging the catheter tube in the receptacle, and connecting the receptacle to the connector to close the opening.

23 Claims, 10 Drawing Sheets

(56) References Cited

U.S. PATENT DOCUMENTS

| | | | |
|---|---|---|---|
| 7,066,912 B2 * | 6/2006 | Nestenborg | A61M 25/002 206/364 |
| 2001/0001443 A1 | 5/2001 | Kayerod et al. | |

FOREIGN PATENT DOCUMENTS

| | | |
|---|---|---|
| EP | 1 277 454 A1 | 1/2003 |
| GB | 2 319 507 A | 5/1998 |
| JP | 63-19149 A | 1/1988 |
| JP | 02-114046 | 9/1990 |
| JP | 2000-281144 A | 10/2000 |
| JP | 2001-500414 A | 1/2001 |
| JP | 2001-190639 A | 7/2001 |
| JP | 2001-299875 A | 10/2001 |
| WO | WO-97/26937 A1 | 7/1997 |
| WO | WO 98/11932 | 3/1998 |
| WO | WO 00/16843 | 3/2000 |
| WO | WO 00/30575 A1 | 6/2000 |
| WO | WO-00/47494 A1 | 8/2000 |
| WO | WO-01/43807 A1 | 6/2001 |
| WO | WO-01/52763 A1 | 7/2001 |

\* cited by examiner

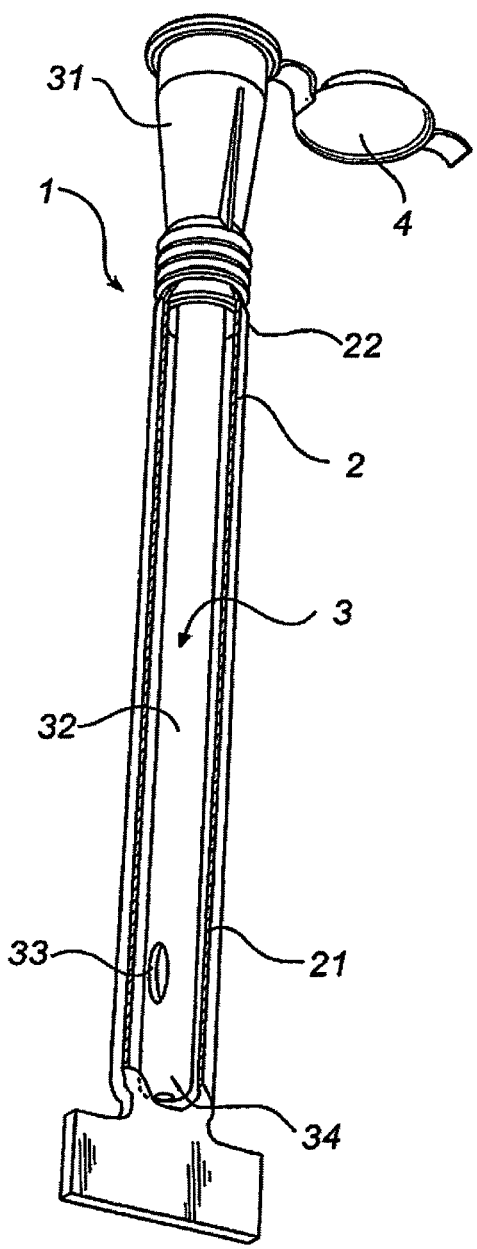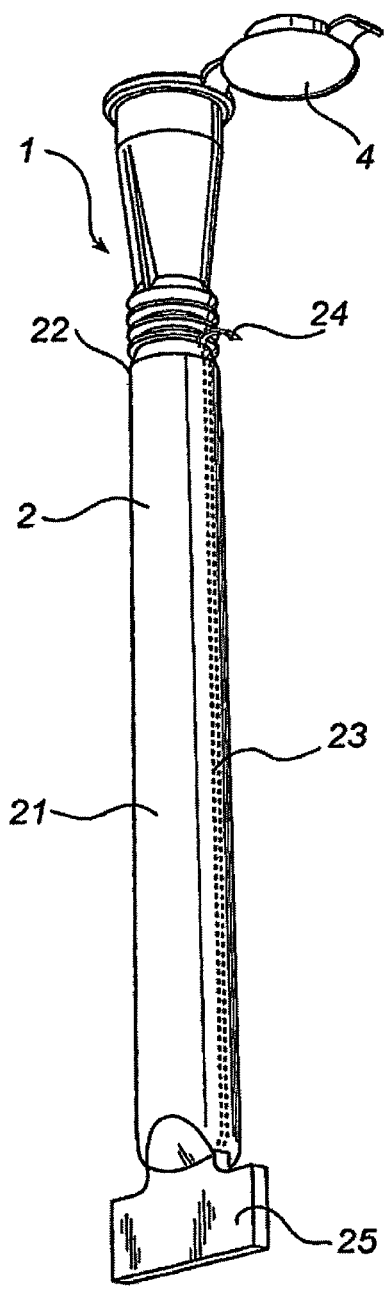
Fig. 1a
Fig. 1b

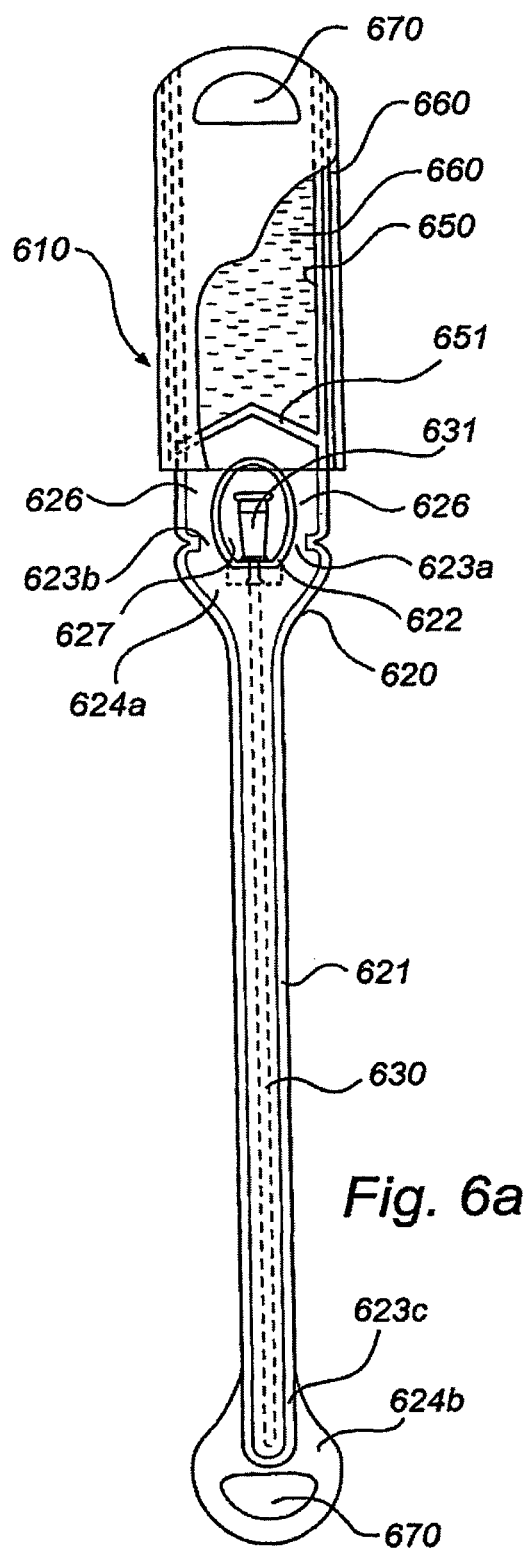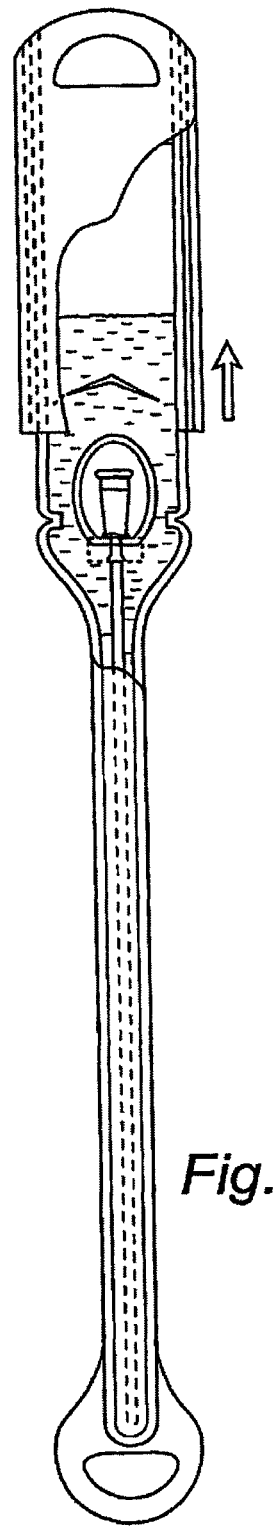
Fig. 6a
Fig. 6b

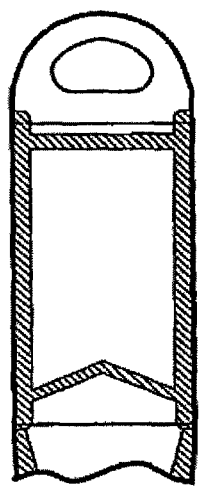 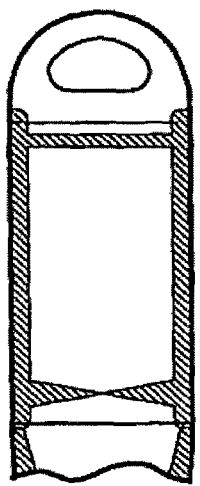 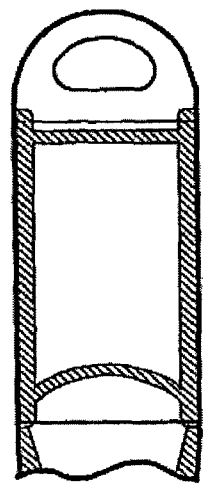
*Fig. 10a*  *Fig. 10b*  *Fig. 10c*
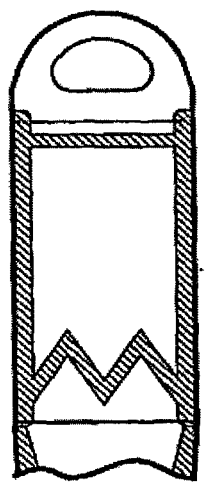 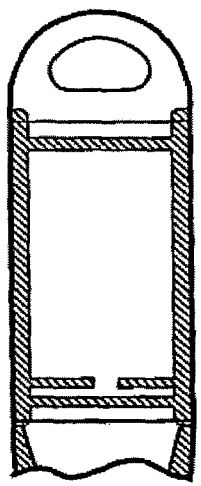 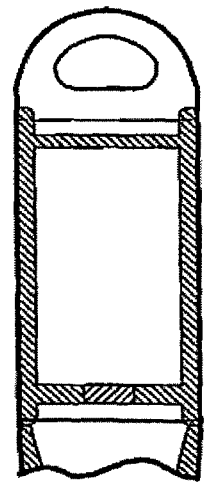
*Fig. 10d*  *Fig. 10e*  *Fig. 10f*

CATHETER ASSEMBLY

This application is a divisional of U.S. application Ser. No. 10/487,912, filed Apr. 27, 2004 now U.S. Pat. No. 8,740,863, which is the national phase under 35 U.S.C. §371 of PCT International Application No. PCT/SE03/00681 which has an International filing date of Apr. 29, 2003, which designated the United States of America and which claims priority on Swedish Patent Application No. 0201330-8, filed Apr. 30, 2002. The entire contents of which are incorporated by reference herein.

FIELD OF THE INVENTION

The present invention relates to a catheter assembly comprising a catheter and a receptacle for accommodation of at least part of the catheter. The invention further relates to a method for producing such a catheter assembly.

BACKGROUND OF THE INVENTION

Catheters find their use in many different medical applications, such as urinary catheters for bladder drainage. Catheters are normally pre-packed in a receptacle by the manufacturer, in order to maintain the catheter in a clean and preferably sterile condition. However, a problem with such catheter assemblies are that they are bulky, making them difficult and expensive to store, transport and handle. Further, a lot of packaging and wrapping material is required, making the assemblies expensive and harmful to the environment.

Urinary catheters in general need to have a lubricant applied to the outer surfaces thereof to facilitate insertion into the urethra. Especially, for lubrication purposes hydrophilic urinary catheters may have a hydrophilic outer surface coating which should be wetted by a fluid such as water or saline for a certain time period prior to insertion thereof into the urethra of a patient. In order to facilitate the use and to improve cleanliness of the catheter, the assemblies have in recent years developed to comprise a rupturable wetting fluid pouch or container as well. This is e.g. known from WO 98/19729. However, unfortunately the inclusion of such a wetting fluid container makes the above-described problem with bulkiness, etc, even more severe.

Further, there has recently been a trend towards so-called "ready-to-use" catheters, where the catheter is arranged in the receptacle together with a wetting fluid, so that the catheter is maintained in a wetted, activated condition. Such a catheter assembly is e.g. known from WO 00/47494. However, in such a catheter, a relatively large amount of wetting fluid is required to fill the receptacle to a certain degree and to ensure that an adequate wetting of the catheter is maintained. accordingly, even this type of catheter assembly suffers from the bulkiness discussed above, and is further relatively heavy. Further, a problem with this type of catheter assemblies are that the catheter becomes wet and slippery, which makes it uncomfortable and difficult to handle.

There is further a problem with known catheter assemblies that the catheter must normally be removed from the receptacle or package before it could be connected to other devices, such as drainage tubes, urine bags, etc. Hereby, the handling of the catheter becomes more difficult, since more work has to be done by the person responsible for the catheterization, and especially during the stressed situation when the catheter is exposed to the environment, instead of in advance, or even as a step during the production process. Further, the time period when the catheter is exposed, and accordingly vulnerable to contamination and the like, is prolonged, which increases the risk for the patient.

Accordingly, there is a need for a leaner and less bulky catheter assembly and/or a catheter assembly which is easier and more convenient to handle and/or a catheter assembly which is less expensive to produce, and especially for hydrophilic urinary catheters. The present invention therefore proposes to address this need. This object is achieved with the catheter assembly and the method according to the appended claims.

SUMMARY OF THE INVENTION

According to one aspect of the invention, it relates to a catheter assembly comprising a catheter including a catheter tube and a connector arranged in one end of the catheter tube; and a catheter receptacle for accommodation of at least the catheter tube. Further, the receptacle is provided with an opening, said opening being connected to and closed by the connector of the catheter.

The term "connector" is, in the context of this application, to be understood in a broad sense, meaning any part of the catheter functioning as a means for connecting the catheter tube to external means, such as external tubing, or simply functioning as an outlet for drainage through the catheter tube. Further, the connector need not be a separate part of the catheter, but could be integrated with the catheter tube.

Further, "end of the catheter", is in the context of this application, also to be understood in a broad sense, meaning the end section of any part projecting or protruding from the rest of the catheter. Consequently, a catheter may have more than two ends, and an end must not be positioned farthest away from the main body of the catheter in any direction.

With the catheter assembly according to the first aspect of the invention, a very advantageous catheter assembly is provided. Generally, the invention relates to a catheter assembly, comprising a catheter receiving receptacle and a catheter having a connector at one end thereof, wherein the receptacle is sealed by said connector. Since the receptacle is closed by the connector of the catheter, only part of the catheter is enclosed in the receptacle. Hereby, the assembly could be made leaner and less bulky since a receptacle of smaller volume could be used, and at the same time less material is required making the assembly easier and less costly to manufacture. This also makes the product more environment friendly, since less material is required. Still, all parts of the catheter intended to be inserted into the patient, i.e. all insertable parts of the catheter, could nonetheless be kept in a sterile and medically safe condition, making this catheter assembly at least as reliable as previously known catheter assemblies where the whole catheter is arranged inside the receptacle.

Further, by the arrangement with the receptacle being closed by the connector of the catheter, whereby at least part of the connector can be accessed from the outside of the receptacle, the catheter could be connected to other devices, such as drainage tubes, urine bags, etc. before removal of the catheter from the receptacle or package. Hereby, the handling of the catheter becomes both simpler and safer, since the connection work need not be done by the person responsible for the catheterization, and especially not during the stressed situation when the catheter is removed from the receptacle and, thus, exposed to the environment. Hereby, the catheterization becomes easier and more efficient, and the time period when the catheter is exposed, and accordingly vulnerable to contamination and the like, is also shortened significantly, which decreases the risk for the patient.

The connection of the catheter to other parts could, with the inventive concept, even be made already during production. Hereby, the production could comprise a module system, where the catheter assembly could be produced as a standard component, which is connectable during production with other parts, such as drainage tubes, urine bags and the like, into different end products. Hereby, the production could be made simpler and more cost efficient, requiring less production machinery, less storages, etc. Hereby, the production also becomes more environment friendly.

Consequently, the invention relates to a catheter assembly comprising a catheter, part of which forms an insertable length to be inserted through a body opening; and a catheter receptacle for accommodation of at least part of the catheter. Further, the receptacle is connected to the catheter, thereby enclosing the insertable length of the catheter, but leaving at least part of the catheter outside the receptacle.

Further, by the arrangement of at least part of the connector outside the receptacle, the catheter could be connected to other devices, such as drainage tubes, urine bags, etc. before removal of the catheter from the receptacle or package.

Some preferred embodiments of the above-discussed aspect of the invention will now be discussed briefly. Preferably, the receptacle is sealingly connected to the catheter, and/or the compartment formed by the receptacle and the catheter is sealed. Hereby, at least an insertable part of the catheter could be maintained in a clean, and preferably sterile, condition during storage. Alternatively or additionally, the compartment formed by the receptacle and the catheter could form a microbial barrier against the environment.

The catheter is preferably a hydrophilic catheter. A hydrophilic catheter is a catheter in which the catheter has, on at least a part of its surface, a hydrophilic surface layer intended to be wetted with a wetting fluid prior to use in order to provide a low-friction surface.

In case a hydrophilic urinary catheter is used in the catheter assembly, the assembly could further comprise a wetting fluid. Hereby, no additional wetting fluid is needed for activation of the catheter, which entails many advantages. For example, activation of the catheter could easily be accomplished in places where it is normally difficult to find an appropriate wetting fluid for this specific use. Further, it could be ensured that only a sufficiently clean and sterile fluid is used, thereby decreasing the risk for unwanted contamination of the catheter. Still further, the wetting of the catheter may be accomplished in a simpler and more convenient manner.

In one line of embodiments, the catheter assembly comprises a container containing the wetting fluid, said container being arranged to keep the wetting fluid separated from at least the insertable part of the catheter during storage and the container being openable for activation of the catheter. In such an embodiment, the wetting fluid may be kept separated from the insertable part of the catheter, i.e. the part of the catheter to be inserted through a body opening of the patient, until the time when the catheter is intended to be used. Then, the wetting fluid container may be opened, e.g. by application of a pressure, a pulling force or the like to the container, whereby the wetting fluid is allowed to discharge into the compartment housing the catheter. The container may be a compartment integrated with the receptacle, or a separate container. In case a separate container is used, said container may be arranged completely inside the receptacle, partly inside the receptacle or outside the receptacle but preferably with some sort of fluid communication with the receptacle.

In another line of embodiments, the catheter assembly comprises a container containing the wetting fluid, said container being formed by a compartment of the receptacle housing the catheter, for preservation of the hydrophilic surface layer in a wetted state during accommodation in said receptacle and provision of a so called "ready-to-use" catheter assembly. In such an embodiment, the catheter is continuously maintained in an activated, ready-to-use condition.

In all embodiments where the catheter assembly comprises a wetting fluid container, the amount of wetting fluid provided is preferably sufficient for filling the receptacle to a certain degree and to ensure that an adequate wetting of the catheter is maintained.

In case the container is a compartment formed by the receptacle and the catheter, said compartment is preferably gas sealed, wherein the longevity of the product is increased. For the same reason, the receptacle is preferably gas impermeable.

A suitable wetting fluid is sterile water or a saline solution.

It is further preferred that the receptacle of the catheter assembly forms an elongate pocket.

The receptacle could be connected to the catheter by means of a welding joint, said joint preferably being arranged between the catheter and the receptacle. This is a simple and cost effective way of providing a tight and sufficiently strong connection. Alternatively, the receptacle could be connected to the catheter by means of a shrink fit, which is also a simple and cost effective way of providing a tight and sufficiently strong connection. The receptacle is preferably connected to the connector of the catheter.

The receptacle of the catheter assembly preferably comprises opening means for opening of the receptacle, said opening means preferably being arranged in an end of the receptacle being opposite to the connection between the receptacle and the catheter. Hereby, unpacking of the catheter before use becomes very easy. The opening means could comprise a peel-off joint, a tear line or the like.

A typical sterilizing agent which could be used for sterilizing the catheter assembly of the invention is ethylene oxide. Moreover, the fluid in the fluid container would normally already be sterile when packed. For these reasons, the wetting fluid container is preferably made of a material which is impermeable or substantially impermeable to ethylene oxide as well as the fluid contained therein. Non-limiting examples of materials satisfying this condition when the fluid is water or saline are aluminium foil laminate, poly(vinylidene chloride) or a laminate comprising metallised film such as metallised poly(ethylene terepthalate), or a silicon oxide coated film, or a laminate comprising aluminum oxide. Other sterilization processes could of course be used instead, for example by irradiation. Steam treatment may also be used for sterilization.

According to another aspect of the invention, it relates to a method for producing a catheter assembly, comprising: providing a receptacle having an opening; providing a catheter including a catheter tube and a connector arranged on one end thereof; arranging the catheter tube in the receptacle; and connecting the receptacle to the connector, thereby closing said opening.

With a production method according to this aspect of the invention, similar advantages are achieved as discussed above in relation to the first and second aspect of the invention.

Preferably, the catheter is first assembled by connecting the catheter tube and the connector, where after the catheter tube is arranged in the receptacle and the receptacle is connected to the catheter connector. However, the manufacturing may also be in a reversed order. E.g. the connector may be connected to the receptacle before assembly of the connector and the catheter tube. In this case, the catheter tube may e.g. be introduced from another opening of the receptacle, which is subsequently closed.

According to another aspect of the invention, it relates to a catheter assembly comprising: a catheter having on at least part of its surface a hydrophilic surface layer intended to produce a low-friction surface character of the catheter by treatment with a wetting fluid prior to use of the catheter; a catheter receptacle forming a cavity for accommodation of at least part of the catheter; and a compartment accommodating said wetting fluid, wherein said compartment forms an integrated part of the receptacle, but being separated from said cavity. Further, an additional outer layer is attached to the receptacle, said layer being arranged to at least partly cover the part of the receptacle forming said wetting fluid compartment.

In accordance with this aspect of the invention, an additional cover is provided in order to achieve a stronger and preferably gas impermeable wetting fluid compartment. Due to the use of this additional cover, the requirements on the material of the receptacle could be lowered, and the material need e.g. not be gas-impermeable. Hereby, the additional cover could provide the impermeability of the compartment wall necessary to alleviate evaporation and maintain the wetting fluid in the compartment during storage. At the same time, only a limited amount of cover material is needed, making the product cost effective to produce.

The additional cover may also be used as a protection for the wetting fluid against a sterilizing agent used for the sterilization of the catheter and the rest of the catheter assembly. A typical sterilizing agent which could be used for sterilizing the wetting apparatus of the invention is ethylene oxide. Moreover, the fluid in the fluid container would normally already be sterile when packed, and need not be further sterilized. Additionally, the sterilizing agent may leave unwanted residual products in the wetting fluid if exposed to the same. For these reasons, it is preferred that the additional cover of the wetting fluid container is made of a material which is impermeable or substantially impermeable to ethylene oxide as well as the fluid contained therein. Non-limiting examples of materials satisfying this condition when the fluid is water or saline are aluminium foil laminate, poly(vinylidene chloride) or a laminate comprising metallised film such as metallised poly(ethylene terephthalate), or a silicon oxide coated film, or a laminate comprising aluminum oxide. Other sterilization processes could of course be used instead, for example by irradiation in which case the fluid in the container could be sterilized in situ at the same time as the rest of the components of the assembly. Steam treatment may also be used for sterilization.

The additional cover may be attached to the compartment by means of an adhesive, welding or any other suitable connection means.

According to a corresponding aspect, the invention further relates to a method for producing a catheter assembly, comprising: providing a receptacle; providing a hydrophilic catheter; arranging at least part of the catheter tube in a cavity of the receptacle; arranging a wetting fluid in a compartment forming an integrated part of the receptacle, but being separated from said cavity; and attaching an additional outer layer to the receptacle to at least partly cover the part of the receptacle forming said wetting fluid compartment.

According to this method, similar advantages as discussed above are achieved.

According to another aspect of the invention, it relates to a catheter assembly comprising: a catheter having on at least part of its surface a hydrophilic surface layer intended to produce a low-friction surface character of the catheter by treatment with a wetting fluid prior to use of the catheter; a catheter receptacle forming a cavity for accommodation of at least part of the catheter; and a compartment accommodating said wetting fluid, wherein said compartment forms an integrated part of the receptacle, but being separated from said cavity, wherein the separation between the wetting fluid compartment and the cavity accommodating the catheter provides a rupturable sealed closure. Further, said closure is provided with at least one point of weakness, in order for an induced rupture to occur in a predetermined position, thereby enabling fluid communication between the compartment and the cavity housing the catheter.

In accordance with this embodiment of the invention, a rupture of the fluid compartment could be effectively controlled, in order for it to occur in a predetermined position. Hereby, it could be avoided that the compartment, upon application of pressure or the like, is ruptured in a random position, which could lead to leakage of the fluid, insufficient wetting of the hydrophilic surface, etc. Instead, the rupture will always occur in the most effective position, leading to an effective wetting of the catheter surface.

Preferably, the closure is formed by a rupturable joint between the compartments, and most preferably the joint is a welded joint with a welding width variation, or a welding strength variation, thus providing the at least one point of weakness. Alternatively, the joint could be arranged in a non-linear arrangement, thus providing the at least one point of weakness. In this case, the joint could be arranged with at least one knee directed towards the wetting fluid compartment. The knee could e.g. have an angled peak portion directed towards the wetting fluid compartment, with an obtuse or acute angle. However, the knee may alternatively have an curved peak portion directed towards the wetting fluid compartment. Hereby, effective rupture control may be achieved, and at the same time a very cost effective and easily producible joint is provided.

According to a corresponding aspect of the invention, a method is provided for producing a catheter assembly, comprising: providing a receptacle; providing a hydrophilic catheter; arranging at least part of the catheter tube in a cavity of the receptacle; arranging a wetting fluid in a compartment forming an integrated part of the receptacle, but being separated from said cavity; and attaching an additional outer layer to the receptacle to at least partly cover the part of the receptacle forming said wetting fluid compartment.

All the various detailed embodiments and different features discussed above in relation to different aspects of the invention discussed above are also usable together with the other aspects of the invention, and thus combinable in other ways than those specifically disclosed, if nothing else is explicitly stated.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

By way of example embodiments of the invention will now be described with reference to the accompanying drawings in which:

FIG. 1 illustrates a first embodiment of a catheter assembly according to the invention, where FIG. 1a is a partly broken view and FIG. 1b is an unbroken view;

FIG. 6 illustrates a sixth embodiment of a catheter assembly according to the invention, where FIG. 6a is a side view of the whole catheter assembly, and FIG. 6b is a view of the catheter assembly of FIG. 6a illustrating the activation process;

FIG. 7 illustrates a seventh embodiment of a catheter assembly according to the invention, where

FIG. 10 illustrates different examples of a weakened joint separating a wetting fluid compartment and a compartment housing the catheter in the receptacle.

DESCRIPTION OF PREFERRED EMBODIMENTS

Figure 2:
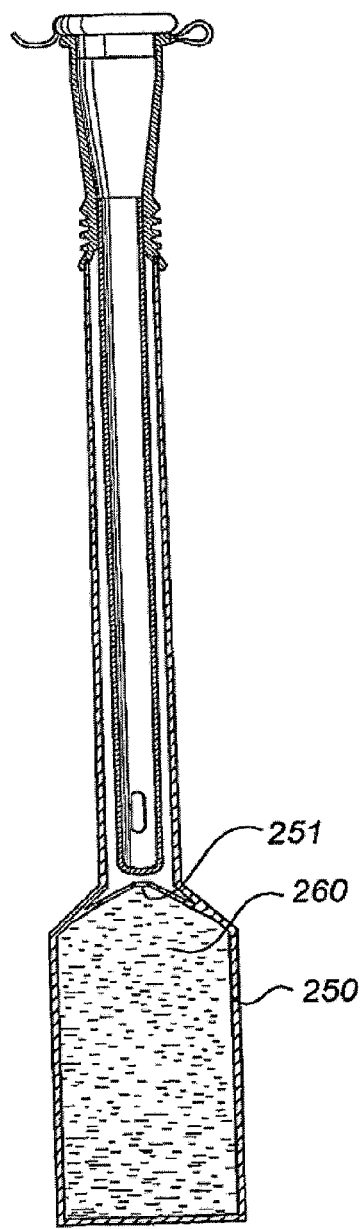
FIG. 2 is a partly broken side view of a second embodiment of a catheter assembly according to the invention.

In the following detailed description preferred embodiments of the invention will be described. However, it is to be understood that features of the different embodiments are exchangeable between the embodiments and may be combined in different ways, unless anything else is specifically indicated.

General Description of the Catheter Assembly and Embodiments with Externally Accessible Connector Referring first to FIG. 1, a first embodiment of a catheter assembly 1 according to the invention comprises a wetting receptacle or bag 2, preferably of a transparent flexible plastics material. The receptacle 2 has a downwardly extending elongate pocket 21 at the forward end and an opening end 22.

The catheter assembly 1 further comprises a catheter, and preferably a hydrophilic urinary catheter 3, having a preferably flared rearward portion 31, an elongate shaft or tube 32 projecting forwardly from the rearward portion 31 and an open-ended lumen (not shown) which extends from the rear end of the rearward portion 31 to a drainage aperture 33 in the rounded tip 34. The rearward portion 31 could function as a connector of the catheter 3, being connectable to other devices such as a urine collection bag, a drainage tube or the like. At least a part of the elongate tube 32 forms an insertable length to be inserted through a body opening of the user, such as the urethra in case of a urinary catheter. By insertable length is normally, in the context of a hydrophilic catheter, meant the length of the elongate tube 32 which is coated with a hydrophilic material, for example PVP, and which could be inserted into the urethra of the patient. Typically, this will be 80-140 mm for a female patient and 200-350 mm for a male patient.

The catheter receptacle 2 is adapted for accommodation of the catheter tube 32 in the elongate pocket 21, and the opening of the opening end 22 is connected to and closed by the connector or rearward end 31 of the catheter. Hereby, the receptacle 2 encloses at least the insertable length of the catheter 3, but leaves a part of the catheter 3 outside the receptacle.

The receptacle 2 preferably forms a sealed compartment around the accommodated part of the catheter 3. Such a sealed compartment could be provided by sealingly connecting the receptacle 2 to the catheter 3 and to close the lumen opening.

The receptacle 2 could be connected to the catheter 3 in various ways. For example, the connection could be provided by means of a welding joint arranged between the catheter and the receptacle. However, it is also possible to connect the receptacle 2 to the catheter 3 by means of a shrink fit, an adhesive or the like. In the disclosed embodiment, the receptacle 2 is arranged on the outward side of the connector 31. However, the connector 31 may comprise a lower end protruding over a part of the elongate tube 32 of the catheter 3, and in such a case the receptacle 2 may alternatively be connected to the inward side of said protruding part.

In the disclosed embodiment, the catheter lumen is closable be means of a cap or cover 4 arranged to sealingly close the connector opening. However, other ways of providing a closure of the lumen are feasible as well, such as arranging a breakable membrane somewhere in the lumen.

The receptacle 2 preferably comprises opening means for facilitating opening of the receptacle in order to expose the catheter 3 for use. The opening means could comprise a tear line 23 connected to a gripping handle 24, such as a pulling tab. Hereby, the user could pull the gripping handle 24, and thereby tearing open the side wall of the receptacle. Additionally, or alternatively, a gripping handle may be arranged in the opposite end of the tear line. However, alternative opening means are also feasible, such as tear-lines arranged in different fashions, peel-off joints, etc. It is also possible to construct the receptacle so that it is openable by a screwing or twisting action, e.g. by screwing or twisting open the end part of the receptacle being opposite to the connector.

The receptacle preferably comprises a plate-like member 25, to be used as a handle and gripping means. Such a member may also be used for carrying printed information, such as one or several of the following: a user instruction, product name, batch number, producer identification, etc. In the disclosed embodiment, this plate-like member is arranged in the end of the receptacle 2 being opposite to the catheter connector 31.

In a method of wetting the catheter 3 according to this embodiment, the user opens the catheter compartment, i.e. the compartment of the receptacle housing the catheter, and applies a wetting fluid onto the insertable end for wetting of the catheter, thereby activating it for catheterization. Different ways of wetting the catheter are feasible. For example, the assembly 1 may be opened in the connector end, by removing the cap 4, whereafter the wetting fluid may be introduced through the catheter lumen. After the activation, the receptacle 2 may be teared opened in order to expose the catheter for insertion into a patient. Alternatively, the receptacle 2 may be opened directly whereby the catheter 3 is exposed and the wetting fluid may be applied directly onto the catheter surface.

Being opened, the receptacle could either be ripped off and then disposed of, or be maintained connected to the catheter. In case the receptacle is intended to be ripped of, areas of weakness could be arranged to facilitate the removal of the receptacle. The receptacle could either be separated from the catheter at the connection between the catheter and the receptacle, or be teared apart, in which case a part of the receptacle will remain connected to the catheter.

When activated and with at least its distal end removed from the receptacle 2, the catheter 3 could then be inserted into the urethra of the patient.

With reference to FIG. 2, a second embodiment of the catheter assembly will now be discussed. In this embodiment, the catheter assembly generally corresponds to the first embodiment. However, in this embodiment the assembly also comprises a wetting fluid container 250 containing a wetting fluid 260. The wetting fluid container is formed in a separate compartment of the receptacle, and between the wetting fluid holding compartment and the compartment holding the catheter, a rupturable separation wall 251 is arranged. The separation wall may be provided by arranging a peelable joint between the compartments.

At least the part of the receptacle forming the wetting fluid container 250 is preferably gas sealed and formed by a gas impermeable material. For example one or several of the following gas impermeable materials could be used: aluminium foil laminate, poly(vinylidene chloride) or laminate comprising a metallised film, such as metallised poly(ethylene terepthalate), or silicon oxide coated film, or a laminate comprising aluminum oxide.

The wetting fluid is preferably sterile water or a saline solution.

In a method of wetting the catheter according to this embodiment, the user applies a compressing force to the wetting fluid container 250 in such a way that the rupturable separation wall is opened and wetting fluid is introduced into the catheter compartment. Preferably, the wetting fluid container 250 contains a sufficient amount of wetting fluid for the insertable length of the catheter to be sufficiently wetted.

After release of the wetting fluid into the catheter compartment the receptacle could be opened, where after the catheter could be exposed and used for catheterization. The receptacle could either be ripped off and then disposed of, or be maintained connected to the catheter.

Figure 3:
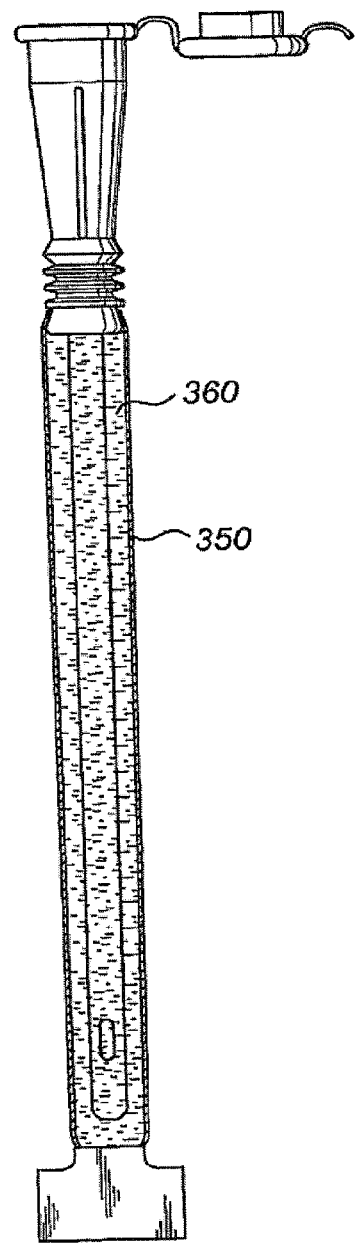
FIG. 3 is a partly broken side view of a third embodiment of a catheter assembly according to the invention.

With reference to FIG. 3, a third embodiment of the catheter assembly will now be discussed. In this embodiment, the catheter assembly generally corresponds to the second embodiment in that it also comprises a wetting fluid container 350 containing a wetting fluid 360. In this case, however, the wetting fluid container 360 is not formed in a separate compartment of the receptacle, but is integrated with the compartment holding the catheter. Hereby, the catheter is activated already during production, and is then maintained in a activated, ready-to-use condition. Thus, in this embodiment, the hydrophilic surface layer is preserved in a wetted state during accommodation in the receptacle and a ready-to-use catheter assembly is provided. In order to preserve this wetted condition the compartment formed by the receptacle and the catheter is preferably gas sealed, and further, the receptacle is preferably gas impermeable.

In use, the receptacle is simply opened, and the catheter could immediately be introduced into the patient.

Figure 4:
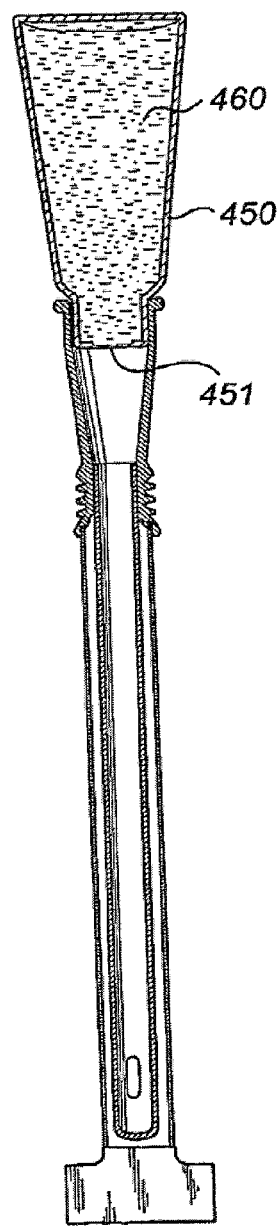
FIG. 4 is a partly broken side view of a fourth embodiment of a catheter assembly according to the invention.

With reference to FIG. 4, a fourth embodiment of the catheter assembly will now be discussed. In this embodiment, the catheter assembly generally corresponds to the second embodiment in FIG. 2 in that it also comprises a wetting fluid container 450 containing a wetting fluid 460. In this case, however, the wetting fluid container 450 is formed in a separate compartment being separated from, and arranged outside the receptacle. The fluid container 450 is arranged on the connector, and a fluid connection between the fluid container and the catheter compartment is prevented by a rupturable separation wall 451. The separation wall could e.g. be a breakable or peelable membrane wall arranged over an opening of the fluid container. The separation wall could be arranged to be broken upon application of a twist, a compression, a pull or the like on the fluid container. The fluid container is preferably sealingly arranged in the opening end of the connector, thereby also functioning as a cover to maintain the catheter compartment in a sealed condition. It is also possible to arrange the rupturable separation wall 451 connected to the connector of the catheter, in which case the wall e.g. may be broken by depressing the fluid container further into the connector.

In a method of wetting the catheter according to this embodiment, the user applies e.g. a compressing force to the wetting container in such a way that the rupturable separation wall is opened and wetting fluid is introduced into the catheter compartment through the catheter lumen. Preferably, the wetting container contains a sufficient amount of wetting fluid for the insertable length of the catheter to be sufficiently wetted.

After release of the wetting fluid into the catheter compartment, the fluid container 450 could be discarded and the receptacle could be opened, where after the catheter could be exposed and used for catheterization. The receptacle could either be ripped off and then disposed of, or be maintained connected to the catheter.

Figure 5A:
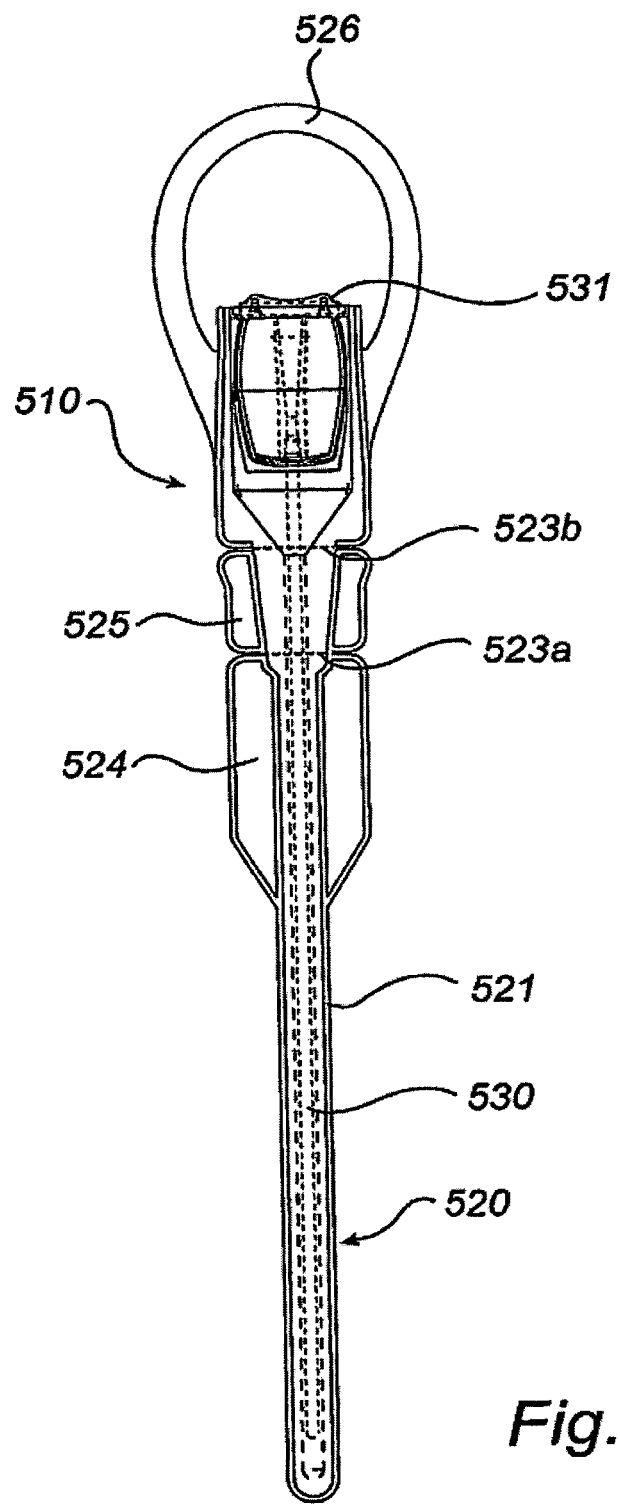
FIG. 5a is a side view of the whole catheter assembly.
Figure 5B:
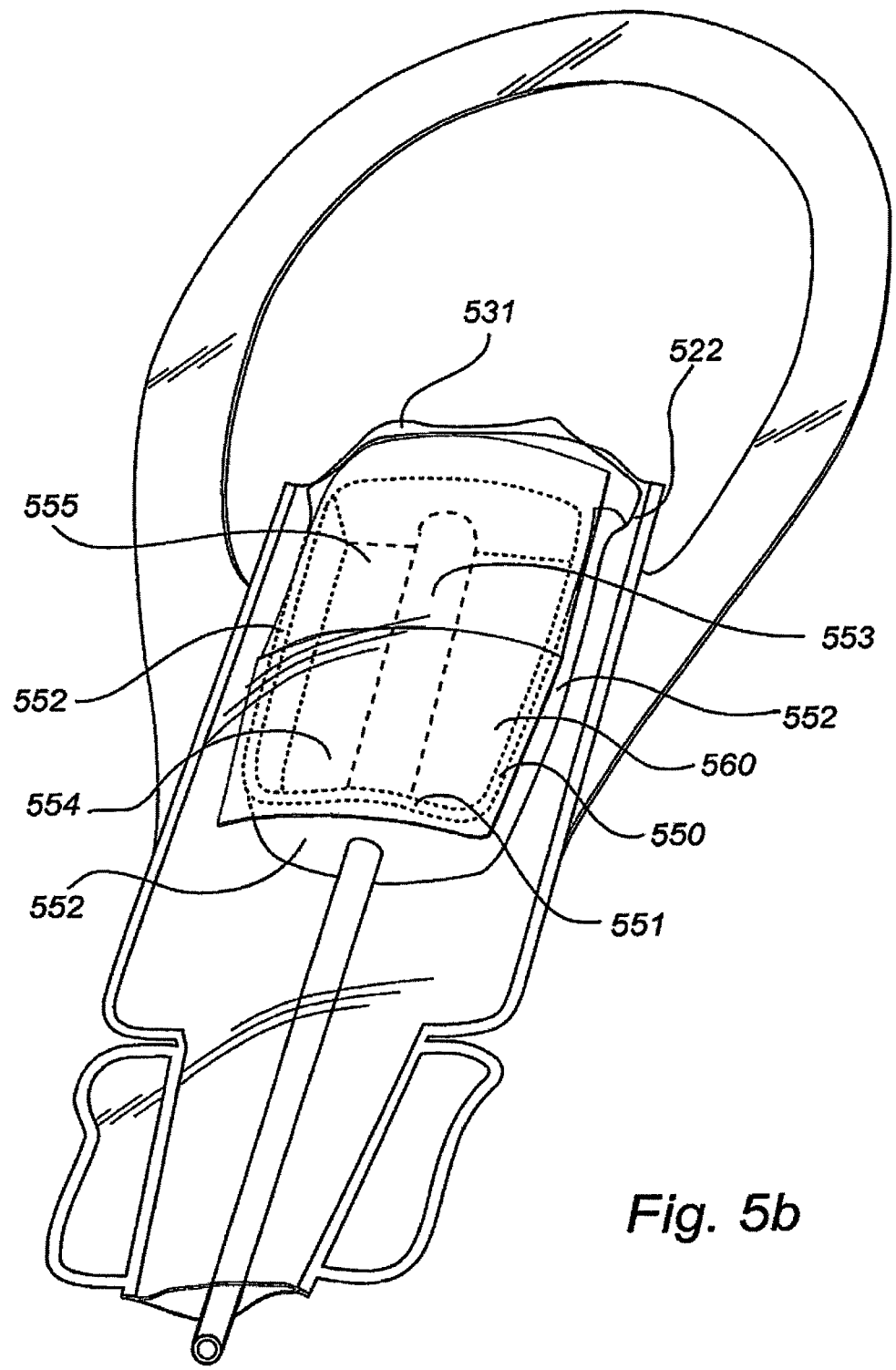
FIG. 5b is an expanded view of the connector part of the catheter assembly shown in FIG. 5a, and FIG. 5c is a view of the connector part of FIG. 5b illustrating the activation process.

With reference to FIG. 5, a fifth embodiment of the catheter assembly will now be discussed. In this embodiment, the catheter assembly 510 comprises a wetting receptacle or bag 520, preferably of a transparent flexible plastics material. The receptacle 520 has a downwardly extending elongate pocket 521 at the forward end and an opening end 522 (see FIG. 5b).

As in the previously discussed embodiments, the catheter assembly 510 further comprises a catheter, and preferably a hydrophilic urinary catheter 530. However, in this case a different type of connector 531 is used, with a different type of connection interface for connection to other devices, such as a urine collection bag a drainage tube or the like.

The catheter receptacle 520 is adapted for accommodation of the catheter tube in the elongate pocket 521, and the opening of the opening end 522 is connected to and closed by the connector or rearward end 531 of the catheter. Hereby, the receptacle encloses at least the insertable length of the catheter 530, but leaves at least part of the catheter outside the receptacle, said part comprising the connection interface.

As discussed previously, the lumen could be closable by means of a cap or cover arranged to sealingly close the connector opening. However, in this embodiment it is preferred that a breakable membrane is arranged somewhere in the lumen, and preferably close to the connection interface. Hereby, the membrane could be arranged to break automatically when connecting the connector to corresponding connection unit of a device to be connected to the catheter.

In this embodiment the assembly also comprises a wetting fluid container 550 containing a wetting fluid 560. In this case, the wetting fluid container is formed in a compartment being integrated with the connector. Preferably at least some of the compartment walls 520 are integrated in connector unit, whereas at least one wall 510 is formed by the receptacle. The wall formed by the receptacle could in this case form the rupturable separation wall.

Figure 5C:
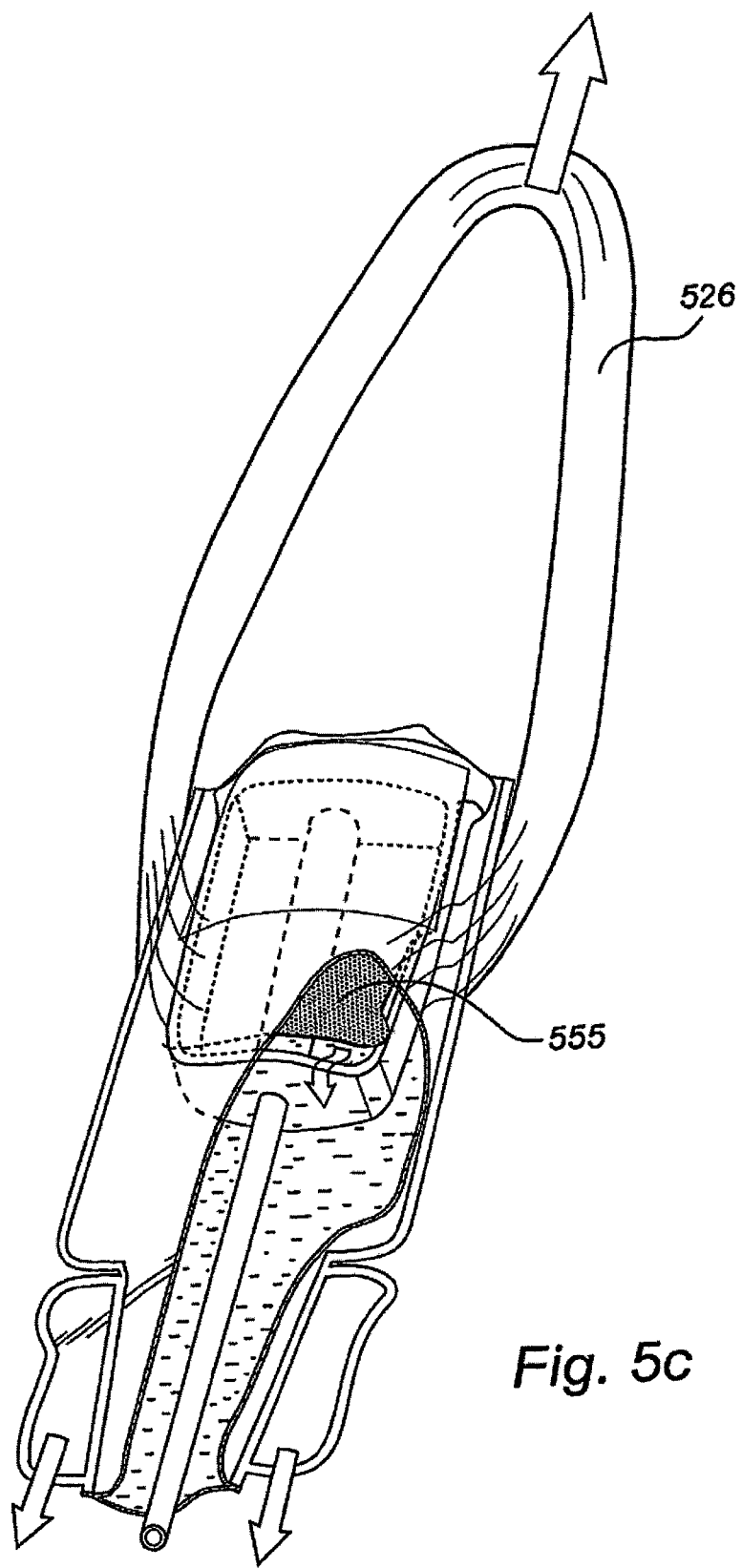
FIG. 5 illustrates a fifth embodiment of a catheter assembly according to the invention, where

In the disclosed embodiment in FIG. 5, one side wall of the wetting fluid container 550 is formed by the wall 531 forming the connection interface and three side walls 552 are formed integrated with the connector and arranged inside the receptacle. Further, one bottom wall 554 is formed integrated with the connector, whereas the top wall is formed as a separation wall formed by the receptacle. In the compartment formed by said walls the wetting fluid is stored. Preferably, the compartment is formed around the catheter lumen, and in that case, a tube 553 is arranged in the compartment for provision of a fluid communication between the connector interface and the elongate tube of the catheter. The wetting fluid container is openable in order to allow the wetting fluid to discharge from the wetting fluid container into the elongate pocket of the receptacle for wetting of the catheter. For example, such an openable container may be provided by making the connection between the separation wall and the rest of the container peelable. Hereby, the separation wall may be peeled opened by applying a relative force between the separation wall and the rest of the container, whereby the wetting fluid is discharged into the rest of the receptacle. The application of such a force may be provided by provision of a handle 526 or the like. In that case, a pulling force may be applied to the handle 526 in relation to the rest of the receptacle, whereby the separation wall 555 is peeled open from the container. This is illustrated schematically in FIG. 5c.

Even in this embodiment the receptacle comprises opening means for facilitating opening of the receptacle in order to expose the catheter for use. The opening means could comprise one or several areas of weakness, such as tear lines 523a, 523b connected to one or several gripping handles 524, such as a pulling tab.

To facilitate the removal of the catheter from the receptacle and the insertion into the urethra of the patient, at least one area of weakness 523a, 523b, such as a tear line, is preferably arranged on the receptacle in the area of the elongate pocket arranged to receive the fluid, in which the catheter is placed. Most preferably, two such areas of weakness 523a, 523b are provided, and separated in the lengthwise direction of the receptacle. The intermediate part of the receptacle may be used as an insertion aid for guiding and holding the wetted catheter when it is inserted into the urethra. There is therefore no need to directly handle the catheter 530 for insertion thereof into the urethra, which is an advantage as the outer surface of the catheter 530 will be slippery due to the wetting procedure and therefore difficult to grip and furthermore because the possibility of contamination of the catheter 503 at this stage is avoided, whereby the cleanness and sterility of the catheter may be maintained.

Pulling tabs 524, 525 may be arranged on one or both sides of the area of weakness, in order to facilitate tearing open of the receptacle.

In a method of wetting the catheter according to this embodiment, the user applies e.g. a pulling force to the handle 526, thereby peeling open the separation wall 555 and discharging the wetting fluid into the catheter compartment. Preferably, the wetting fluid container contains a sufficient amount of wetting fluid for the insertable length of the catheter to be sufficiently wetted.

After release of the wetting fluid into the catheter compartment the receptacle may be opened and part of it may even be used as an applicator, as is discussed above.

With reference to FIG. 6, a sixth embodiment of the catheter assembly will now be discussed. In this embodiment, the catheter assembly 610 comprises a wetting receptacle or bag 620, preferably of a transparent flexible plastics material. The receptacle 620 has a downwardly extending elongate pocket 621 at the forward end and an opening part 622 with an opening.

As in the previously discussed embodiments, the catheter assembly further comprises a catheter, and preferably a hydrophilic urinary catheter 630, with a connection interface for connection to other devices, such as a urine collection bag a drainage tube or the like. The catheter receptacle 620 is adapted for accommodation of the catheter tube in the elongate pocket 621, and the opening of the opening part 622 is connected to and closed by the connector 631 or rearward end of the catheter. Hereby, the receptacle encloses at least the insertable length of the catheter, but leaves at least part of the catheter outside the receptacle, said part comprising the connection interface.

As discussed previously, the lumen could be closable by means of a cap or cover arranged to sealingly close the connector opening. However, in this embodiment it is preferred that a breakable membrane is arranged somewhere in the lumen, and preferably close to the connection interface. Hereby, the membrane could be arranged to break automatically when connecting the connector to corresponding connection unit of a device to be connected to the catheter.

The assembly also comprises a wetting fluid container 650 containing a wetting fluid 660. In this case, the wetting fluid container is formed in a compartment of the receptacle being separated from the compartment accommodating the catheter. The wetting fluid container 650 is in this embodiment arranged in a part of the receptacle extending rearwardly from the catheter, i.e. behind the connector part of the catheter. Said rearward part of the receptacle is preferably in fluid communication with the forward part housing the catheter. This fluid communication may be provided by the arrangement of at least one channel 626 past the catheter connector. Preferably, two such channels 626 are arranged, one on each side of the connector. Thereby the receptacle frames an opening 627 in which the protruding part of the catheter is situated.

The wetting fluid compartment of the receptacle is separated from the compartment holding the catheter by means of a rupturable separation wall 651. The separation wall 651 may be formed by a separable joint between the compartments, such as weld of less strength than the other welds forming the compartment. Hereby, the wetting fluid may be discharged into the other compartment of the receptacle by compressing the wetting fluid container, or by applying a pulling force between the end parts of the assembly.

In order to achieve a stronger and preferably gas impermeable wetting fluid compartment, it is preferred to arrange an additional cover 660 around said compartment. This additional cover could be arranged on the inside of the compartment formed in the receptacle, but is preferably arranged as an outer cover arranged over the wetting fluid compartment part of the receptacle. Such an additional cover is very advantageous, and this concept is discussed in more detail later.

Even in this embodiment the receptacle could comprise opening means for facilitating opening of the receptacle in order to expose the catheter for use. The opening means could comprise one or several areas of weakness, such as tear lines 623a, 623b connected to one or several gripping handles 624a, such as a pulling tab. Said opening means could be used to facilitate the removal of the catheter from the receptacle and the insertion into the urethra of the patient.

Further, alternatively or additionally, opening means may be arranged close to the distal end of the catheter. Said opening means may comprise a peelable joint 623c connected to tabs 624b extending from the edge for enabling opening by peeling the tabs apart, thereby separating the foil walls of the receptacle. Preferably, the receptacle is arranged to allow a significant degree of separation of the foil walls, thereby making it possible to expose an essential part, and preferably the whole, insertable part of the catheter during this opening process. There is therefore no need to directly handle the catheter 630 during the insertion thereof into the urethra, which is an advantage as the outer surface of the catheter 630 will be slippery due to the wetting procedure and therefore difficult to grip, and furthermore because the possibility of contamination of the catheter at this stage is avoided, whereby the cleanness and sterility of the catheter may be maintained.

At least one, and preferably both, of the end parts of the catheter assembly are preferably provided with gripping means, such as openings 670, for facilitating handling of the catheter assembly.

In a method of wetting the catheter according to this embodiment, the user applies e.g. a compressing force to the wetting fluid compartment 650, thereby forcing open the separation joint 651 and discharging the wetting fluid into the catheter compartment, as is illustrated in FIG. 6*b*. Preferably, the wetting fluid container contains a sufficient amount of wetting fluid for the insertable length of the catheter to be sufficiently wetted.

After release of the wetting fluid into the catheter compartment the receptacle may be opened, e.g. at the distal end, as is discussed above, for insertion of the catheter.

Figure 7A:
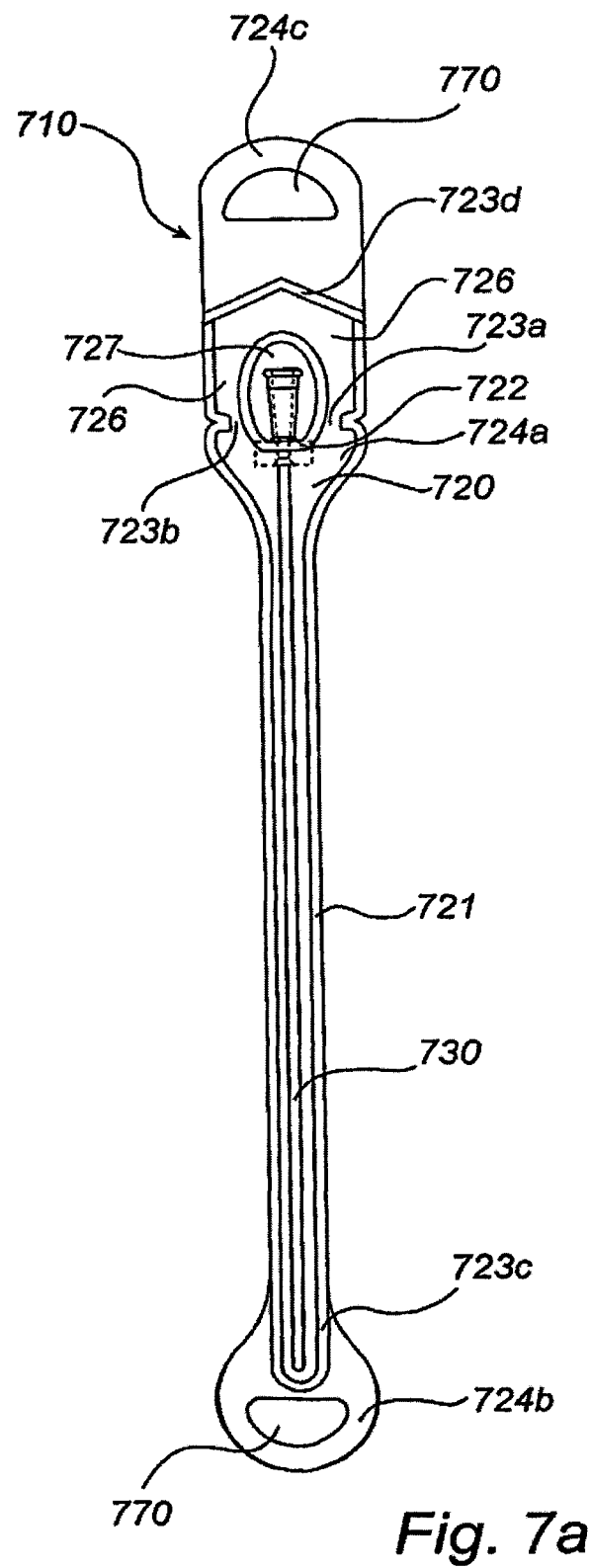
FIG. 7a is a side view of the whole catheter assembly.

With reference to FIG. 7, a seventh embodiment of the catheter assembly will now be discussed. In this embodiment, the catheter assembly 710 comprises a wetting receptacle or bag 720, preferably of a transparent flexible plastics material. The receptacle 720 has a downwardly extending elongate pocket 721 at the forward end and an opening part 722 with an opening.

As in the previously discussed embodiments, the wetting apparatus further comprises a catheter, and preferably a hydrophilic urinary catheter 730, with a connection interface for connection to other devices, such as a urine collection bag a drainage tube or the like. The catheter receptacle is adapted for accommodation of the catheter tube in the elongate pocket 721, and the opening of the opening part 722 is connected to and closed by the connector or rearward end of the catheter. Hereby, the receptacle encloses at least the insertable length of the catheter, but leaves at least part of the catheter outside the receptacle, said part comprising the connection interface.

As discussed previously, the lumen could be closable by means of a cap or cover arranged to sealingly close the connector opening. However, as in the sixth embodiment it is preferred that a breakable membrane is arranged somewhere in the lumen, and preferably close to the connection interface.

Even in this embodiment the receptacle could comprise opening means for facilitating opening of the receptacle in order to expose the catheter for use. The opening means could comprise one or several areas of weakness, such as tear lines 723*a*, 723*b* connected to one or several gripping handles 724*a*, such as a pulling tab. Said opening means could be used to facilitate the removal of the catheter from the receptacle and the insertion into the urethra of the patient Further, alternatively or additionally, opening means may be arranged close to the distal end of the catheter. Said opening means may comprise a peelable joint 723*c* connected to tabs 724*b* extending from the edge for enabling opening by peeling the tabs apart, thereby separating the foil walls of the receptacle. Preferably, the receptacle is arranged to allow a significant degree of separation of the foil walls, thereby making it possible to expose an essential part, and preferably the whole insertable part of the catheter during this opening process. There is therefore no need to directly handle the catheter 730 for insertion thereof into the urethra, which is an advantage as the outer surface of the catheter will be slippery due to the wetting procedure and therefore difficult to grip and furthermore because the possibility of contamination of the catheter at this stage is avoided, whereby the cleanness and sterility of the catheter may be maintained.

At the other end of the receptacle, preferably arranged relatively close to proximal end of the catheter, further opening means may be arranged, comprising e.g. a peelable joint 723*d* connected to tabs 724*c* extending from the edge for enabling opening by peeling the tabs apart, thereby separating the foil walls of the receptacle. Said opening means may be used for the provision of a wetting fluid introduction opening for introduction of a wetting fluid into a wetting fluid receiving compartment of the receptacle when the catheter is to be wetted and activated before use.

The opening means for providing the wetting fluid introduction opening is preferably arranged in a part of the receptacle extending rearwardly from the catheter, i.e. behind the connector part of the catheter. Said rearward part of the receptacle is preferably in fluid communication with the forward part housing the catheter. This fluid communication may be provided by the arrangement of at least one channel 726 past the catheter connector. Preferably, two such channels 726 are arranged, one on each side of the connector. Thereby the receptacle frames an opening 727 in which the protruding part of the catheter is situated. With this constructional arrangement, the wetting fluid introduction opening could be made relatively large, which facilitates the introduction of the wetting fluid.

At least one, and preferably both, of the end parts of the catheter assembly are preferably provided with gripping means, such as openings 770, for facilitating handling of the catheter assembly.

Figure 7B:
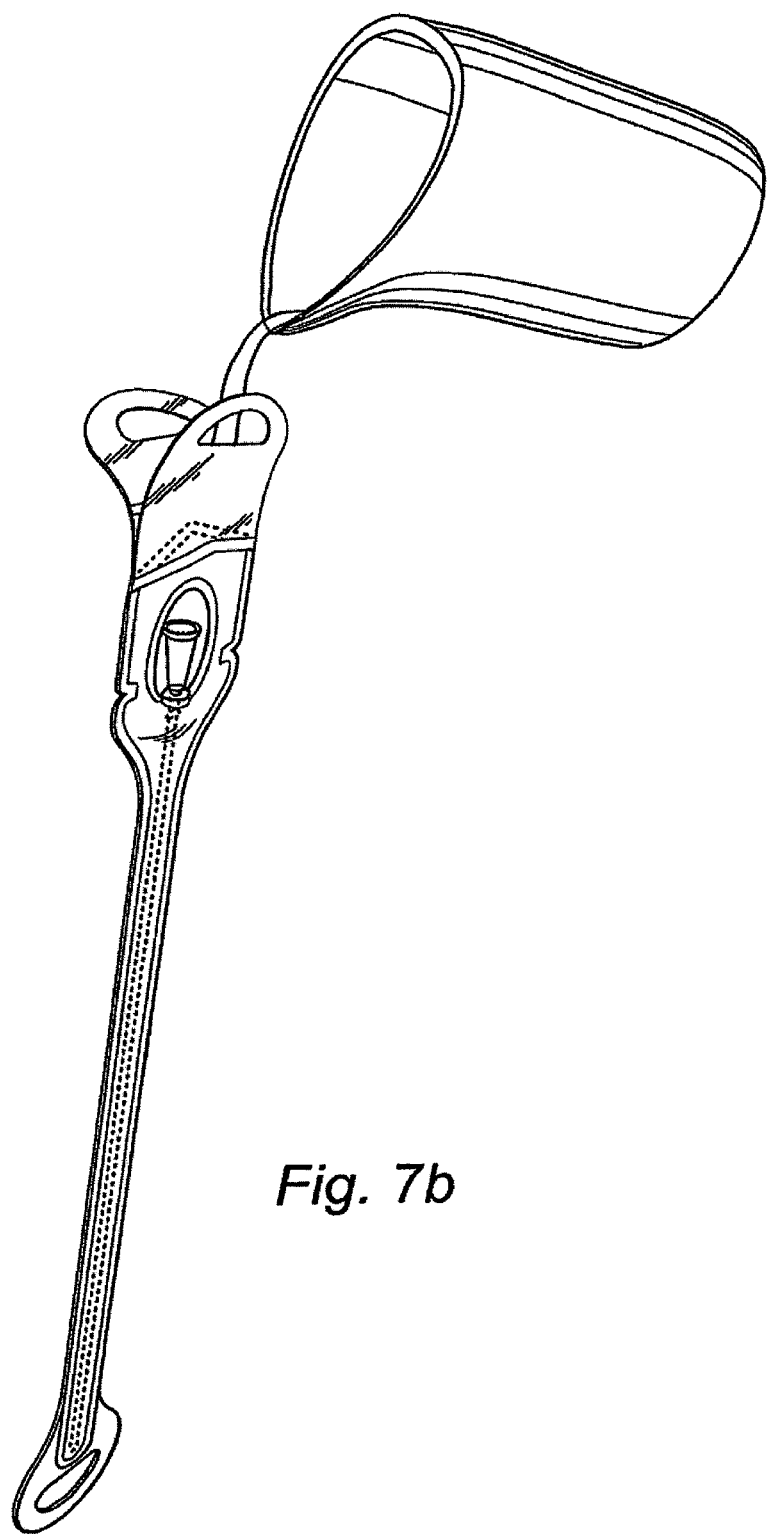
FIG. 7b is a view of the catheter assembly of FIG. 7a illustrating the activation process.

In a method of wetting the catheter according to this embodiment, the user opens the wetting fluid introduction opening by pulling the tabs 724*c* apart, thereby forcing open the peelable joint 723*d*. Thereafter, a wetting fluid could easily be introduced into the catheter compartment, as is illustrated in FIG. 7*b*.

After introduction of the wetting fluid into the catheter compartment the receptacle may be opened further, e.g. at the distal end, as is discussed above, for insertion of the catheter into the patient.

The catheter assemblies as discussed above could be sterilized using ethylene oxide. In case the assembly comprises a container with a wetting fluid, such as sterile water or saline, there sterilizing of the contents of the container is normally both unnecessary and unwanted. Accordingly, the material of the container is preferably impermeable to ethylene oxide and water. Non-limiting examples of materials meeting these requirements are poly(vinylidene chloride) (PVDC), aluminium foil laminates or a laminate comprising a metallised film, for example metallised poly(ethylene terepthalate), or a silicon coated film. Other sterilization processes could of course be used instead, for example by irradiation in which case the fluid in the container could be sterilized in situ at the same time as the rest of the components of the assembly. Steam treatment may also be used for sterilization.

Production of the different catheter assemblies discussed above is relatively simple. Basically, the production method comprises the steps of providing a receptacle having an opening and a catheter. Thereafter, the catheter is partly introduced into the receptacle, and the receptacle is connected to the catheter, thereby closing said opening, with at least a part of the catheter protruding out from the receptacle.

In the assemblies discussed above, the receptacle may actually be regarded as a receptacle where part of the receptacle is formed by a part of the catheter. However, this is not applicable for the examples described with reference to FIG. 8-10, discussed in the following.

Catheter Assemblies Having a Wetting Fluid Container with Additional Cover

As is already discussed above with reference to FIG. 6, the arrangement of an additional cover 660 around the wetting fluid compartment of the receptacle is advantageous.

This additional cover could be arranged on the inside of the compartment formed in the receptacle, but is preferably arranged as an outer cover arranged over the wetting fluid compartment part of the receptacle. Due to the use of this additional cover, the requirements on the material of the receptacle could be lowered, and the material need e.g. not be gas-impermeable. Hereby, the additional cover could provide the impermeability of the compartment wall necessary to alleviate evaporation and maintain the wetting fluid in the compartment during storage.

The additional cover may also be used as a protection for the wetting fluid against a sterilizing agent used for the sterilization of the catheter and the rest of the catheter assembly. A typical sterilizing agent which could be used for sterilizing the wetting apparatus of the invention is ethylene oxide. Moreover, the fluid in the fluid container would normally already be sterile when packed, and need not be further sterilized. Additionally, the sterilizing agent may leave unwanted residual products in the wetting fluid if exposed to the same. For these reasons, it is preferred that the additional cover of the wetting fluid container is made of a material which is impermeable or substantially impermeable to ethylene oxide as well as the fluid contained therein. Non-limiting examples of materials satisfying this condition when the fluid is water or saline are aluminium foil laminate, poly(vinylidene chloride) or a laminate comprising metallised film such as metallised poly(ethylene terepthalate), or a silicon oxide coated film, or a laminate comprising aluminum oxide, The additional cover may be attached to the compartment by means of an adhesive, welding or any other suitable connection means.

Accordingly, in a production method of this catheter assembly, the receptacle is manufactured, and the catheter is arranged in the receptacle, as is discussed in more detail below. Further, the wetting fluid is introduced into the wetting fluid compartment, and the additional cover is arranged outside said compartment. Then, the assembly could be sterilized, whereby the additional cover serves as a protection for the wetting fluid against the sterilizing agent.

The additional cover as discussed above could also be used for other types of catheter assemblies, such as assemblies where the catheter is fully enclosed in the receptacle, or where the connector of the catheter is arranged in a separate compartment of the receptacle.

Figure 8:
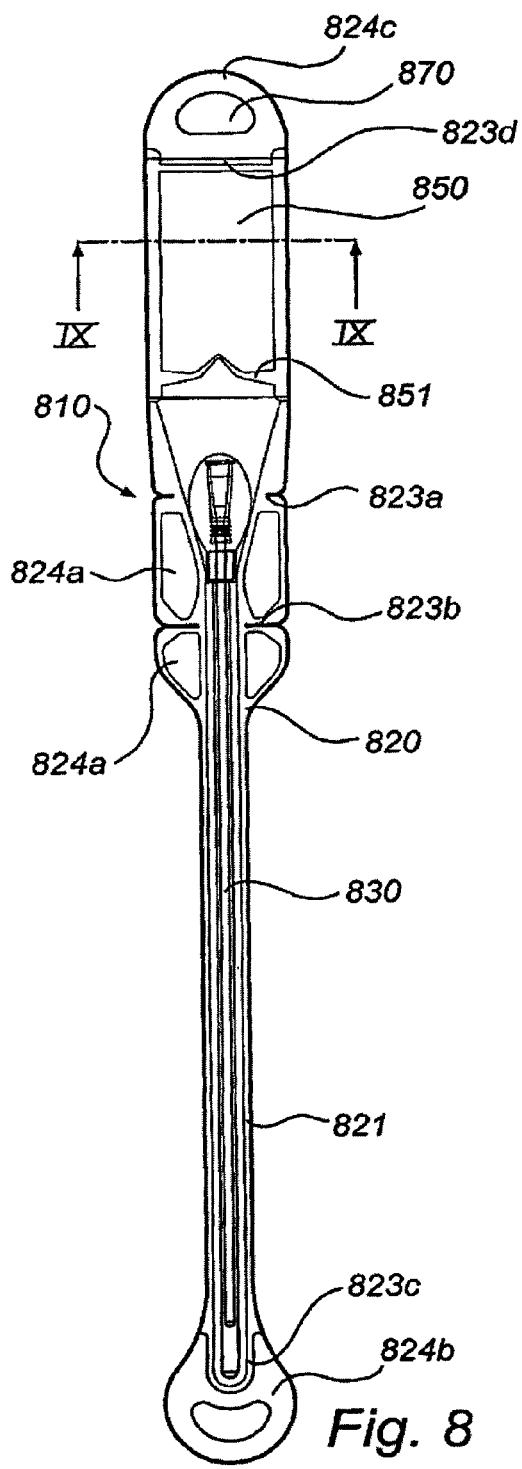
FIG. 8 is a partly broken side view of a eight embodiment of a catheter assembly according to the invention.
Figure 9:
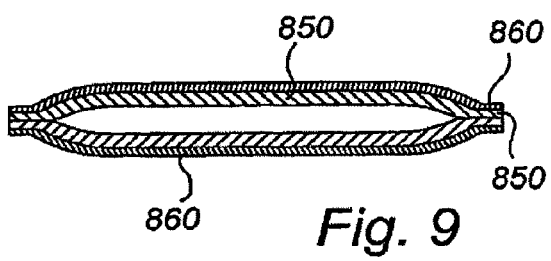
FIG. 9 is a cross-section through the line IX-IX in FIG. 8.

With reference to FIG. 8, an eight embodiment of the catheter assembly will now be discussed. This embodiment to a large extent resembles the embodiment discussed with reference to FIG. 6. The most important differences between the embodiments in FIG. 8 and FIG. 6 are that the whole catheter is enclosed in the receptacle in the embodiment in FIG. 8, and that the wetting fluid compartment is configured somewhat differently.

In this embodiment, the catheter assembly 810 comprises a wetting receptacle or bag 820, preferably of a transparent flexible plastics material. The receptacle 820 has a downwardly extending elongate pocket 821 at the forward end.

As in the previously discussed embodiments, the catheter assembly further comprises a catheter, and preferably a hydrophilic urinary catheter 830, with a connection interface for connection to other devices, such as a urine collection bag a drainage tube or the like. The catheter receptacle 820 is adapted for accommodation of the catheter, and at least the catheter tube is accommodated in the elongate pocket 821. Hereby, the receptacle in this embodiment encloses the whole length of the catheter.

The assembly also comprises a wetting fluid container 850 containing a wetting fluid (not illustrated). The wetting fluid container is formed in a compartment of the receptacle being separated from the compartment accommodating the catheter. The wetting fluid container 850 is in this embodiment arranged in a part of the receptacle extending rearwardly from the catheter, i.e. behind the connector part of the catheter. Said rearward part of the receptacle is preferably in fluid communication with the forward part housing the catheter. This fluid communication may be provided by the compartment of the receptacle housing the catheter being rearwardly open towards the separation to the wetting fluid container.

The wetting fluid compartment of the receptacle is separated from the compartment holding the catheter by means of a rupturable separation wall 851. The separation wall 851 is in this case formed by a separable joint between the compartments, such as is discussed in more detail in the following. Hereby, the wetting fluid may be discharged into the other compartment of the receptacle by compressing the wetting fluid container, or by applying a pulling force between the end parts of the assembly.

In order to achieve a stronger and preferably gas impermeable wetting fluid compartment, an additional cover 860 is arranged around said compartment. This additional cover is arranged as an outer cover arranged over the wetting fluid compartment part of the receptacle. Such an additional cover is very advantageous, and this concept has already been discussed in more detail with reference to FIG. 6.

In this embodiment, two sheets of outer cover material is arranged over the part of the receptacle forming the wetting fluid container. Preferably, the outer cover material sheets are dimensioned essentially only to cover the wetting fluid container part of the receptacle. However, larger sheets, possibly covering the whole receptacle are conceivable, as well as smaller sheets, possibly only covering a part of the wetting fluid compartment. Further, a folded sheet of cover material may be used as an alternative two the two separate sheets discussed above.

The attachment of the outer cover could be provided in different manner, as has already been discussed. In this embodiment, the cover sheets are welded to the receptacle at the ends are of the sheets, as is best visible in the cross-sectional illustration of FIG. 9. Accordingly, the sheets are preferably welded to the receptacle close to the welds forming the receptacle.

Even in this embodiment the receptacle could comprise opening means for facilitating opening of the receptacle in order to expose the catheter for use. The opening means could comprise one or several areas of weakness, such as tear lines 823*a*, 823*b* connected to one or several gripping handles 824*a*, 824*a*', such as a pulling tab. Said opening means could be used to facilitate the removal of the catheter from the receptacle and the insertion into the urethra of the patient.

Further, alternatively or additionally, opening means may be arranged close to the distal end of the catheter. Said opening means may comprise a peelable joint 823*c* connected to tabs 824*b* extending from the edge for enabling opening by peeling the tabs apart, thereby separating the foil walls of the receptacle. Preferably, the receptacle is arranged to allow a significant degree of separation of the foil walls, thereby making it possible to expose an essential part, and preferably the whole, insertable part of the catheter during this opening process. There is therefore no need to directly handle the catheter 830 during the insertion thereof into the urethra.

At the other end of the receptacle, preferably arranged relatively close to proximal end of the catheter but on the other side of the wetting fluid compartment, further opening means may be arranged, comprising e.g. a peelable joint 823*d* connected to tabs 824*c* extending from the edge for enabling opening by peeling the tabs apart, thereby separating the foil walls of the receptacle. Said opening means may be used for the removal of the catheter from the proximal end after the release of the wetting fluid.

At least one, and preferably both, of the end parts of the catheter assembly are preferably provided with gripping means, such as openings 870, for facilitating handling of the catheter assembly.

The method of wetting the catheter according to this embodiment resembles the wetting process discussed with reference to FIG. 6. After release of the wetting fluid into the catheter compartment the receptacle may be opened, e.g. at the distal end, as is discussed above, for insertion of the catheter.

Catheter Assemblies Having a Wetting Fluid Container with Improved Rupture Control A catheter assembly is e.g. disclosed in FIG. 6 as comprising a hydrophilic catheter, a catheter receptacle forming a cavity for accommodation of at least part of the catheter and a compartment accommodating said wetting fluid, wherein said compartment forms an integrated part of the receptacle, but being separated from said cavity. In this type of catheter assembly, it is advantageous if the separation between the wetting fluid compartment and the cavity accommodating the catheter provides a rupturable sealed closure, in which it is provided at least one point of weakness, in order for an induced rupture to occur in a predetermined position, thereby enabling fluid communication between the compartment and the cavity housing the catheter.

In the assembly of FIG. 6, a wetting fluid container 650 is formed in a compartment of the receptacle being separated from the compartment accommodating the catheter. The wetting fluid container 650 is in this embodiment arranged in a part of the receptacle extending rearwardly from the catheter, i.e. behind the connector part of the catheter. Said rearward part of the receptacle is preferably in fluid communication with the forward part housing the catheter. The wetting fluid compartment of the receptacle is separated from the compartment holding the catheter by means of a rupturable separation wall 651. The separation wall 651 may be formed by a separable joint between the compartments, such as weld of less strength than the other welds forming the compartment. Consequently, a whole segment of the total weld joint is weakened, viz. the part of the joint facing the catheter compartment. When a rupture is induced, e.g. by manual compression of the wetting fluid compartment or by applying a pulling force between the end parts of the assembly, the rupture will inevitably occur in this predetermined position, thus ensuring the intended functionality of the catheter assembly product.

In order to achieve an even better control of the rupture process, the area of weakness could be even narrower. It is preferred that the weakness is maximized in a limited number of discrete points, such as in one, two or three maxima. However, the points of weakness may also be evenly distributed over a limited area. In that case, it is preferred if the area of weakness is distributed over less than 10% of the joint length, and more preferably over less than 5%, and most preferably over less than 1%.

In the example of FIG. 6 the weakness has a maximum narrowed down to essentially one point of the length of the joint. This is achieved by means of a non-linear geometrical arrangement of the joint. The joint is here arranged with a knee directed towards the wetting fluid compartment. The knee has an angled peak portion directed towards the wetting fluid compartment, with an obtuse angle. The peak portion defines the area of maximal weakness, and consequently the rupture will inevitably commence in this point, leading to a controllable and predictable rupture process.

In the embodiment discussed above in relation to FIG. 8, a similar arrangement is provided. In this embodiment, the rupturable separation wall 851 is likewise formed by a separable joint between the compartments, whereby the wetting fluid may be discharged into the other compartment of the receptacle by compressing the wetting fluid container, or by applying a pulling force between the end parts of the assembly. In this embodiment this is achieved by means of a non-linear geometrical arrangement of the joint together with a weld width variation. The joint is here arranged with a knee directed towards the wetting fluid compartment. The knee has an angled peak portion directed towards the wetting fluid compartment, with an acute angle. The peak portion defines the area of maximal weakness, and consequently the rupture will inevitably commence in this point, leading to a controllable and predictable rupture process. Further, this effect is supported and increased by an advantageously arranged width variation of the weld. In this embodiment, the width of the weld is at a minimum at the peak area, and gradually increases towards the ends. Hereby, the strength of the weld is at a minimum at the peak-area, coinciding with the separation force being maximized at the same position due to the geometrical arrangement of the weld. Accordingly, the two parameters, weld width and geometrical arrangement, cooperates to form a very predictable and easily ruptured separation wall.

Many different alternatives are conceivable to form the desired rupturable joint between the compartments. Some of these alternatives will now be discussed with reference to FIG. 10.

In FIG. 10*a*, a separation joint is illustrated comprising a knee directed towards the wetting fluid compartment. The knee has an angled peak portion directed towards the wetting fluid compartment, with an obtuse angle. The peak portion defines the area of maximal stress build-up, and accordingly the area of maximal weakness, and consequently the rupture will inevitably commence in this point, leading to a controllable and predictable rupture process.

In FIG. 10*b*, a separation joint is illustrated comprising a width variation of the weld. In this embodiment, the width of the weld is at a minimum essentially at the center of the joint, and gradually increases towards the ends. Hereby, the strength of the weld is at a minimum where the width is the smallest, and consequently the rupture will inevitably commence in this point, leading to a controllable and predictable rupture process.

In FIG. 10*c*, a separation joint is illustrated comprising a knee directed towards the wetting fluid compartment. The knee has a inwardly curved peak portion, directed towards the wetting fluid compartment. The peak portion defines the area of maximal stress build-up, and accordingly the area of maximal weakness, and consequently the rupture will inevitably commence in this point, leading to a controllable and predictable rupture process.

In FIG. 10*d*, a separation joint is illustrated comprising a double knee directed towards the wetting fluid compartment. The joint has two angled peak portion directed towards the wetting fluid compartment, with acute angles. The peak portions defines the area of maximal stress build-up, and accordingly the area of maximal weakness, and consequently the rupture will inevitably commence in one, or both, of these points, leading to a controllable and predictable rupture process.

In FIG. 10e, a separation joint is illustrated comprising two welds, wherein a discontinuity is arranged in one of the welds. In this embodiment, an interruption is arranged in the innermost weld, and essentially in the center of the joint. Hereby, the strength of the joint is at a minimum at the discontinuity area, and consequently the rupture will inevitably commence in this area, leading to a controllable and predictable rupture process.

In FIG. 10f, a separation joint is illustrated comprising a weld comprising different qualities or weld strengths. In this embodiment, a part of the weld is of a poorer quality and less strength that the rest of the weld, and this part is positioned essentially in the center of the joint. Hereby, the strength of the joint is at a minimum at the area of the weaker weld, and consequently the rupture will inevitably commence in this area, leading to a controllable and predictable rupture process.

Naturally, other alternatives are conceivable as well. Further, it is also possible to combine two or more of the alternatives, as is e.g. the case with the embodiment discussed in relation to FIG. 8.

CONCLUSION AND SUMMARY

The invention has now been discussed in relation to different embodiments. However, it should be appreciated by someone skilled in the art that several further alternatives are possible. For example, the features of the different embodiments discussed above could naturally be combined in many other ways. Specifically, the features and details discussed in relation to the different main aspects of the invention are usable also in relation to the other aspects, even though this may not be specifically discussed in the exemplification. Further, the different main aspects of the invention are useable either separately or in various combinations.

Further, different ways of connecting the receptacle with the catheter are possible, such as by welding, different types of adhesives, shrink fits, etc. Further, it is possible to connect the receptacle to the connector or to a part of the catheter tube, as long as the insertable part of the catheter is arranged within the receptacle. In the later case, the catheter need not even have a connector. The catheter may also be arranged to have more than one part at least partly protruding out from the receptacle, such as several connectors.

Further, the catheter need not be a hydrophilic catheter, but other types of catheters may be used as well. In that case, other types of lubricants may be used instead of the wetting fluid discussed in relation to the above-disclosed embodiments. It is further possible to use the invention for other types of catheters than urinary catheters, such as vascular catheters or the like.

In case the catheter assembly comprises a wetting fluid container, it is possible to arrange this container in many different ways. For example, the container may be a separate container. Such a container may be arranged completely inside the receptacle, partly inside the receptacle, or completely outside the receptacle. Alternatively, the wetting fluid container may be an integrated compartment of the receptacle. This compartment may be separated from the compartment housing the insertable part of the catheter, or be integrated with such a compartment. In the latter case, the catheter could be maintained in a wetted, activated state. Further, the wetting fluid container may be arranged close to the distal part of the catheter, close to the proximal part of the catheter, or in any other suitable location in the assembly. In case the wetting fluid is arranged separate from the insertable part of the catheter, the separation wall or joint could e.g. be a breakable or peelable membrane wall, but alternative embodiments are naturally feasible, such as various types of detachable or openable caps or closings. The wetting fluid container could be arranged to be discharged upon application of a twist, a compression, a pull or the like on the fluid container. Preferably the wetting fluid could be discharged without breaking or rupturing the receptacle, even though this may not be necessary, depending on the intended use, etc.

Still further, the means for opening of the receptacle could be any suitable opening means, such as tear lines, peelable joints, breakable areas of weakness, detachable or openable caps or closings, and the like.

Many different materials could also be used for the different parts of the catheter assembly.

Ethylene sterilization could be used for sterilization of the catheter assemblies discussed above. However, many other types of sterilization processes could of course be used instead, for example by irradiation in which case the fluid in the container could be sterilized in situ at the same time as the rest of the components of the assembly. Steam treatment may also be used for sterilization.

It will be appreciated by those versed in the art that several such alternatives similar to those described above could be used without departing from the spirit of the invention, and all such modifications should be regarded as a part of the present invention, as defined in the appended claims.

The invention claimed is:

1. A urinary catheter assembly comprising:
   a catheter comprising a catheter tube, part of which forms an insertable length to be inserted through a body opening, and a connector which has a distinctly different geometrical structure than the catheter tube, and arranged on one end of the catheter tube adapted to connect the catheter to an external element, wherein the catheter is a single-lumen hydrophilic urinary catheter including a hydrophilic surface layer configured to be wetted with a wetting fluid prior to use;
   a catheter receptacle for accommodation of at least part of the catheter,
   wherein the receptacle is directly connected to the connector of the catheter, thereby enclosing the catheter tube, including the insertable length of the catheter, but leaving at least part of the connector of the catheter outside the receptacle,
   wherein the connector includes only a single passage extending therethrough, the passage being formed by a continuous sidewall; and
   a wetting fluid arranged in a compartment of the assembly,
   wherein the connector forms a separate part of the catheter, connected to the catheter tube, and the wetting fluid compartment is integrated with the connector and provided with a rupturable separation wall, whereby the wetting fluid is released into the catheter compartment for wetting of the hydrophilic catheter when the rupturable separation wall is peeled off or broken.

2. The catheter assembly of claim 1, wherein the compartment formed by the receptacle and the catheter forms a microbial barrier towards the environment.

3. The catheter assembly of claim 1, wherein the receptacle is gas impermeable.

4. A method for producing a urinary catheter assembly, comprising:
provautomatic a receptacle having an opening;
providing a catheter including a catheter tube and a connector which has a distinctly different geometrical structure than the catheter tube adapted to connect the catheter to an external element arranged on one end thereof, wherein the catheter is a single-lumen hydrophilic urinary catheter including a hydrophilic surface layer configured to be wetted with a wetting fluid prior to use, and wherein the connector has a connection interface for connection to other devices;
arranging the catheter tube in the receptacle;
directly connecting the receptacle to the connector, thereby closing said opening, but leaving at least part of the connector outside the receptacle, said at least part of the connector including the connection interface;
wherein the connector includes only a single passage extending therethrough, the passage being formed by a continuous sidewall; and
providing a wetting fluid in a wetting fluid compartment integrated with the connector, the wetting fluid compartment comprising a rupturable separation wall, whereby the wetting fluid is released into the catheter compartment for wetting of the hydrophilic catheter when the rupturable separation wall is peeled off or broken.

5. The method of claim 4, wherein the receptacle is connected to the connector thereby sealingly closing the receptacle.

6. A catheter assembly, comprising:
a hydrophilic urinary catheter, part of which forms an insertable length to be inserted through a body opening, said hydrophilic urinary catheter including a hydrophilic surface layer configured to be wetted with a wetting fluid prior to use;
a connector arranged on one end of the catheter adapted to connect the catheter to an external element;
a catheter receptacle forming a first compartment for accommodation of at least an insertable part of the catheter,
wherein the receptacle is connected to the catheter, thereby enclosing the insertable part of the catheter, but leaving at least part of the catheter outside the receptacle; and
a second compartment for housing the wetting fluid for wetting said hydrophilic urinary catheter, said second compartment being arranged to keep the wetting fluid separated from the first compartment during storage, and being adapted to open to discharge the wetting fluid into the first compartment for activation of the catheter, wherein the second compartment is positioned at or in the vicinity of an end of the assembly at which the connector of the catheter is arranged, and being opposite to an insertable tip of the catheter, and in a part of the receptacle extending rearwardly from the catheter, the second compartment thereby being formed behind the connector, and wherein at least one channel is arranged along the side of, but separated from, the connector, thereby providing fluid communication between the first and second compartments.

7. A method for producing a catheter assembly, comprising:
providing a receptacle having an opening;
providing a hydrophilic urinary catheter including a catheter tube and a connector arranged on one end thereof, said hydrophilic urinary catheter including a hydrophilic surface layer configured to be wetted with a wetting fluid prior to use;
arranging the catheter tube in the receptacle;
connecting the receptacle to the connector, thereby closing said opening, wherein the receptacle forms a first compartment for accommodation of at least an insertable part of the catheter; and
providing a second compartment for housing the wetting fluid for wetting said hydrophilic urinary catheter, said second compartment being arranged to keep the wetting fluid separated from the first compartment during storage, and being adapted to open to discharge the wetting fluid into the first compartment for activation of the catheter, wherein the second compartment is positioned at or in the vicinity of an end of the assembly at which the connector of the catheter is arranged, and being opposite to an insertable tip of the catheter, and in a part of the receptacle extending rearwardly from the catheter, the second compartment thereby being formed behind the connector, and wherein at least one channel is arranged along the side of, but separated from, the connector, thereby providing fluid communication between the first and second compartments.

8. A wetted catheter assembly, comprising:
a hydrophilic urinary catheter, part of which forms an insertable length to be inserted into a body opening, said hydrophilic urinary catheter including a hydrophilic surface layer configured to be wetted with a wetting fluid prior to use and extending over the entire insertable length;
a catheter receptacle forming a compartment for accommodation of at least the insertable length of the catheter,
a connector which is a distinctly different structure than the catheter tube, arranged on one end of the catheter adapted to connect the catheter to an external element;
wherein the receptacle is directly connected to the catheter connector, thereby enclosing the insertable length of the catheter, but leaving at least part of the catheter outside the receptacle, and wherein the receptacle is gas impermeable and the compartment is gas sealed; and
the wetting fluid for wetting said hydrophilic urinary catheter also arranged within said compartment, for preservation of the hydrophilic surface layer of at least the insertable length of said hydrophilic urinary catheter in a wetted state while being accommodated in the receptacle,
wherein the entire insertable length of the catheter is maintained immersed in the wetting fluid, whereby the wetted catheter is ready-to-use.

9. A method for producing a catheter assembly, comprising:
providing a receptacle having an opening;
providing a hydrophilic urinary catheter including a catheter tube, part of which forms an insertable length to be inserted into a body opening, and a connector which is a distinctly different structure than the catheter tube, adapted to connect the catheter to an external element arranged on one end thereof, said hydrophilic urinary catheter including a hydrophilic surface layer configured to be wetted with a wetting fluid prior to use and extending over the entire insertable length;
arranging the catheter tube in the receptacle;
connecting the receptacle directly to the connector, thereby closing said opening, whereby the receptacle forms a compartment for accommodation of at least the insertable length of the catheter; and
providing the wetting fluid for wetting said hydrophilic urinary catheter in said compartment, for preservation of the hydrophilic surface layer of at least the insertable length of said hydrophilic urinary catheter in a wetted state while being accommodated in the receptacle, wherein the entire insertable length of the catheter is maintained immersed in the wetting fluid, whereby the wetted catheter is ready-to-use.

10. The catheter assembly of claim 1, wherein the connector has a flared structure.

11. The method of claim 4, wherein the connector has a flared structure.

12. A urinary catheter assembly comprising:
   a catheter, part of which forms an insertable length to be inserted through a body opening, wherein the catheter is a single-lumen hydrophilic urinary catheter including a hydrophilic surface layer configured to be wetted with a wetting fluid prior to use; and
   a catheter receptacle for accommodation of at least part of the catheter, wherein the receptacle is connected to the catheter, thereby enclosing the entire insertable length of the catheter and forming a sealed compartment, but leaving at least part of the catheter outside the receptacle;
   wherein the receptacle is further provided with a tear line in the sidewall extending in the length direction of the catheter and being arranged with a gripping handle for tearing opening of the receptacle, the gripping handle protruding out from a wall of the receptacle at an end of the package being in the vicinity of a connector end of the catheter or a insertable tip of the catheter.

13. A method for producing a urinary catheter assembly, comprising:
   providing a receptacle having an opening;
   providing a catheter including a catheter tube and a connector arranged on one end thereof, wherein the catheter is a single-lumen hydrophilic urinary catheter including a hydrophilic surface layer configured to be wetted with a wetting fluid prior to use;
   arranging the catheter tube in the receptacle; and
   connecting the receptacle to the connector, thereby closing said opening;
   wherein the receptacle is further provided with a tear line extending in the length direction of the catheter and being arranged with a gripping handle for tearing opening of the receptacle, the gripping handle protruding out from a wall of the receptacle at an end of the package being in the vicinity of a connector end of the catheter or a insertable tip of the catheter,
   wherein the receptacle encloses the entire insertable length of the catheter and forms a sealed compartment.

14. The method of claim 6, wherein the hydrophilic surface layer is arranged to cover the entire insertable length of the catheter.

15. The catheter assembly of claim 1, wherein the connector has a connecting end with a diameter larger than a diameter of the catheter tube, and the receptacle is directly connected to the connecting end of the connector.

16. The catheter assembly of claim 1, wherein the connector has a connecting end surrounding and overlapping with the catheter tube, and the receptacle is directly connected to the connecting end of the connector.

17. The catheter assembly of claim 1, wherein at least some of the walls of the wetting fluid compartment are integrated in the connector, whereas at least one wall is formed by the receptacle.

18. The catheter assembly of claim 17, wherein the wall of the wetting fluid compartment being formed by the receptacle forms a rupturable separation wall.

19. The catheter assembly of claim 1, wherein the wetting fluid compartment is formed around the catheter lumen.

20. The catheter assembly of claim 1, wherein at least one of the walls of the wetting fluid compartment forms a separable opening.

21. The catheter assembly of claim 20, wherein a handle is provided connected to the separation wall, arranged to apply a force between the separation wall and rest of the wetting fluid compartment for discharge of the wetting fluid.

22. The catheter assembly of claim 1, wherein the wetting fluid compartment is arranged outside the receptacle.

23. The catheter assembly of claim 8, wherein the gas impermeable receptacle is made of at least one material selected from the group: aluminum foil laminate, poly (viylidene chloride), laminate comprising a metalized film, silicon oxide coated film and a laminate comprising aluminum oxide.

* * * * *